United States Patent [19]

Anderson et al.

[11] 4,371,614

[45] Feb. 1, 1983

[54] *E. COLI* BACTERIA CARRYING RECOMBINANT PLASMIDS AND THEIR USE IN THE FERMENTATIVE PRODUCTION OF L-TRYPTOPHAN

[75] Inventors: David M. Anderson, Rockville, Md.; Klaus M. Herrmann; Ronald L. Somerville, both of West Lafayette, Ind.

[73] Assignee: Ajinomoto Co., Inc., Tokyo, Japan

[21] Appl. No.: 180,296

[22] Filed: Aug. 22, 1980

[51] Int. Cl.³ .......................... C12N 1/00; C12R 1/19; C12N 9/00; C12P 13/22; C12P 21/00; C12N 15/00; C12N 1/20

[52] U.S. Cl. .................................. 435/108; 435/317; 435/849; 435/183; 435/68; 435/172; 435/253

[58] Field of Search ................ 435/108, 172, 317, 253

[56] References Cited

U.S. PATENT DOCUMENTS 4,237,224 12/1980 Cohen et al. .......................... 435/68

OTHER PUBLICATIONS

Tribe and Pittard, Applied and Environmental Microbiology, v. 38, pp. 181–190 (Aug. 1979).
Nagahari et al., Gene 1: 141–152 (1977).
Fredericq and Cornelis, Journal of General Microbiology 105: 357–349 (1978).
Oxender et al. Proceedings of the National Academy of Sciences USA V. 76 5524–5528 (Nov. 1979).
Reznikoff and Thornton, Journal of Bacteriology V. 109: 526–532 (9172).
Collins et al., Proceedings of the National Academy of Sciences USA vol. 73: 3838–3842 (1976).
Enger-Valk et al. Gene 9: 69–85 (1980).
Hershfield et al., Proceedings of the National Academy of Sciences USA V. 71: 3455–3459 (1974).
Wagner Abstract of German Patent DT 2841642 Mar. 1980.
Nagahari et al., Abstract of Mol. Gen. Genet. 171, 115 (1979) Chem. Abstr. 90:200102e (1979).
Hallewell et al. Gene 9, 27–47 (1980).
Somerville et al. Abstract of J. Mol. Biol. 11, 747 (1965) Chem. Abstr. 63:2152d.
Watson, *Molecular Biology of the Gene*, W. A. Benjamin, Inc. (1977), pp. 398–400.
Bertrand et al. Abstract of J. Mol. Biol. 117, 227–247 (1977) in Chem. Abstr. 88:85816k (1978).

*Primary Examiner*—Alvin E. Tanenholtz
*Assistant Examiner*—James Martinell
*Attorney, Agent, or Firm*—Oblon, Fisher, Spivak, McClelland & Maier

[57] ABSTRACT

A bacterium which comprises a host of the genus *Escherichia* deficient in the enzyme tryptophanase carrying a plasmid with genetic information to control L-tryptophan production is useful for the fermentative production of L-tryptophan in high yields.

34 Claims, 4 Drawing Figures

CONSTRUCTION OF PLASMIDS

E. COLI BACTERIA CARRYING RECOMBINANT PLASMIDS AND THEIR USE IN THE FERMENTATIVE PRODUCTION OF L-TRYPTOPHAN

BACKGROUND OF THE INVENTION

1. Field of the Invention

The present invention relates to *E. coli* microorganisms carrying recombinant plasmids constructed in vitro and their use for producing L-tryptophan by fermentation.

2. Brief Description of the Prior Art

The production of L-tryptophan from carbohydrates in wild type microorganism strains, has been obtained in the prior art through artificial mutants therefrom. Among the known examples of such artificial mutants are those of the genera Brevibacterium resistant to 5-methyl-tryptophan (U.S. Pat. No. 3,700,539), *Bacillus* resistant to 5-fluorotryptophan (Japanese Published Unexamined Patent Application Number 20391/1974), and Enterobacter resistant to 5-methyl-tryptophan (Japanese Published Unexamined Patent Application Number 57888/1976).

The most efficient known microorganism to produce tryptophan is *Corynebacterium glutamicum* ATCC 21851, which requires phenyl-alanine and tyrosine, and is resistant to 4-methyl-tryptophan, 6-fluoro-tryptophan, 4-amino-phenylalanine, 4-fluoro-phenylalanine, tyrosine-hydroxamate, and phenylalanine-hydroxamate. This strain produced 16.8 mg/ml tryptophan from 15 g/dl of sugar derived from cane blackstrap molasses. However, the yield of tryptophan in this best known method, is still insufficient to fulfill commercial requirements.

The possibility of utilizing recently developed genetic recombination techniques, to engineer a microorganism capable of producing high levels of tryptophan is appealing. The general techniques for the introduction of genes, and the amplification in bacteria capable of expressing them have recently been described by Gilbert and Villa-Komaroff in Scientific American, 242: 74-94 (1980). Briefly, one or more genes from a donor organism, such as a prokaryotic or eukaryotic cell are introduced into a vector or plasmid (extrachromosomal circular DNA) in vitro, by means of a splicing/ligation sequence using endonuclease and ligase enzymes respectively. The hybrid plasmid containing the gene or genes is then mixed with cells of a host organism, usually a prokaryotic bacterial microorganism. A dilute solution of calcium chloride renders the bacteria permeable and the cells will take up plasmids from solution. Reproduction of the plasmid-carrying host microorganisms then produces millions of identical copies of the recombinant DNA. If the appropriate genetic control sequences are present, the amplified gene or genes will produce corresponding enzymes using the available protein-synthesizing apparatus of the host.

Hershfield et al, for example (Proceedings of the National Academy of Sciences, USA, 71: 3455-3459 (1974)), have reported the insertion of a DNA fragment of *E. coli* possessing genetic information related to tryptophan (trp) production (trpA-E gene), into the Col El (colicinogenic factor El) plasmid. When a tryptophan auxotroph of *E. coli* was transformed with the resulting hybrid plasmid (Col El trp), the tryptophan auxotroph became a tryptophan prototroph. Elevated levels of tryptophan biosynthetic enzymes were reported. These authors however, did not further attempt to maximize tryptophan production, as their aim was solely to demonstrate the utility of the Col El plasmid as a molecular vehicle for cloning and amplification of DNA.

The biosynthetic pathways for the synthesis of aromatic amino acids (tryptophan, tyrosine, phenylalanine) in bacteria, are shown in Chart I:

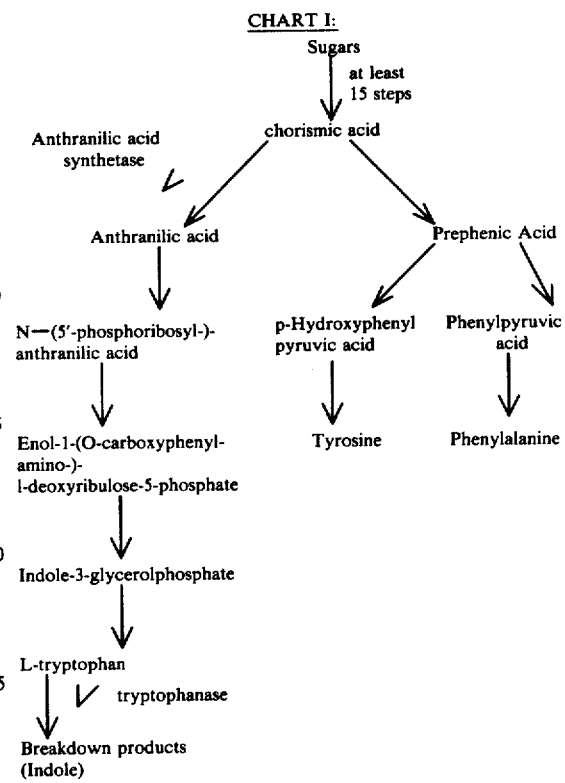

CHART I:

Tyrosine, phenylalanine and tryptophan are produced from a common biosynthetic intermediate, chorismic acid. Tyrosine and phenylalanine are furthermore derived from another common intermediate, prephenic acid. The first major enzyme of the tryptophan pathway is anthranilate synthetase which, in *E. coli* is subject to feedback inhibition by L-tryptophan. The degradation of tryptophan into indole by the enzyme tryptophanase is also shown in Chart I.

A need continues to exist for microorganisms capable of producing high levels of tryptophan. A need also continues to exist for a method for the production of tryptophan in high yields, using a microorganism distinct from those obtained by the mutation techniques of the prior art.

SUMMARY OF THE INVENTION

These and other objects of the invention which will hereinafter become more readily apparent have been attained by providing:

A bacterium which comprises a host of the genus Escherichia deficient in the enzyme tryptophanase, carrying a plasmid with genetic information to control tryptophan production.

Another object of the invention has been attained by providing a method for producing L-tryptophan by fermentation which comprises culturing in a culture medium a bacterium as described hereinbefore, and recovering the L-tryptophan produced from the culture medium.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein.

| Bgl I: | *Bacillus globiggi* |
|---|---|
| Bam HI: | *Bacillus amyloliquefaciens* H |
| EcoR I: | *E. coli* RY13 |
| Pst I: | *Providencia stuartii* 164 |
| Hind III: | *Haemophilus influenzae* Rd |
| Bat E II: | *Bacillus stearotermophilus* ET |
| Hpa I: | *Haemophilus parainfluenzae* |
| Sal I: | *Streptomyces albis* G |
| Xba I: | *Xanthomonas badrii* |
| Sac I: | *Streptomyces achromogenes* |
| Sst I: | *Streptomyces stanford* |
| Bcl I: | *Bacillus caldolyticus* |
| Xho I: | *Xanthomonas holicola* |
| Kpn I: | *Klebsiella pneumoniae* |
| Pvu II: | *Proteus vulgaris* |

Figure 2:
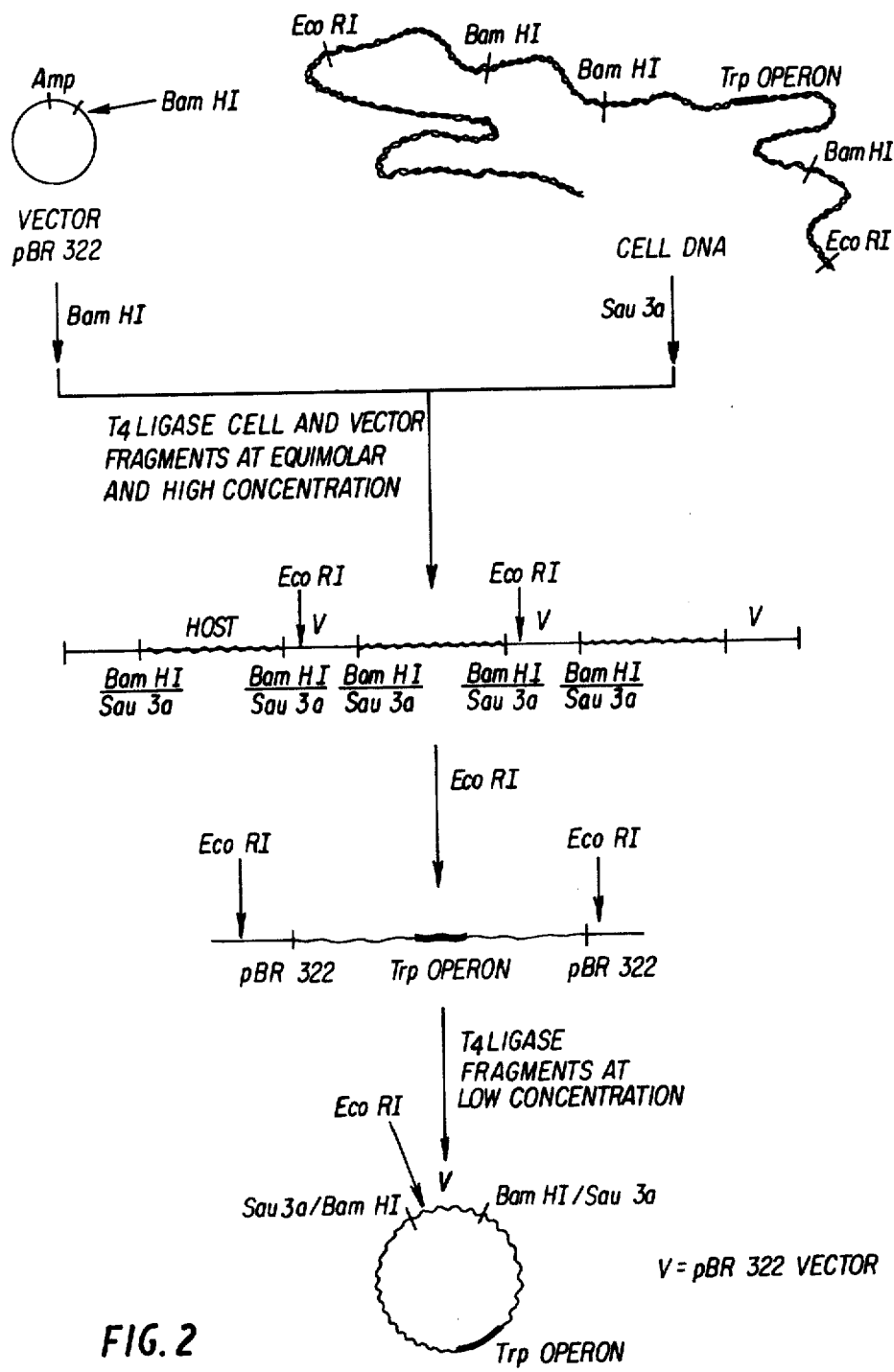

FIG. 2 shows the cloning strategy for $MT^R$ #2 trp genes from cell DNA using the vector pBR322 as cloning vehicle. Abbreviations used:

Sau 3a: endonuclease derived from Staphylococcus aureus 3a

Amp: ampicillin resistance gene

Figure 3:
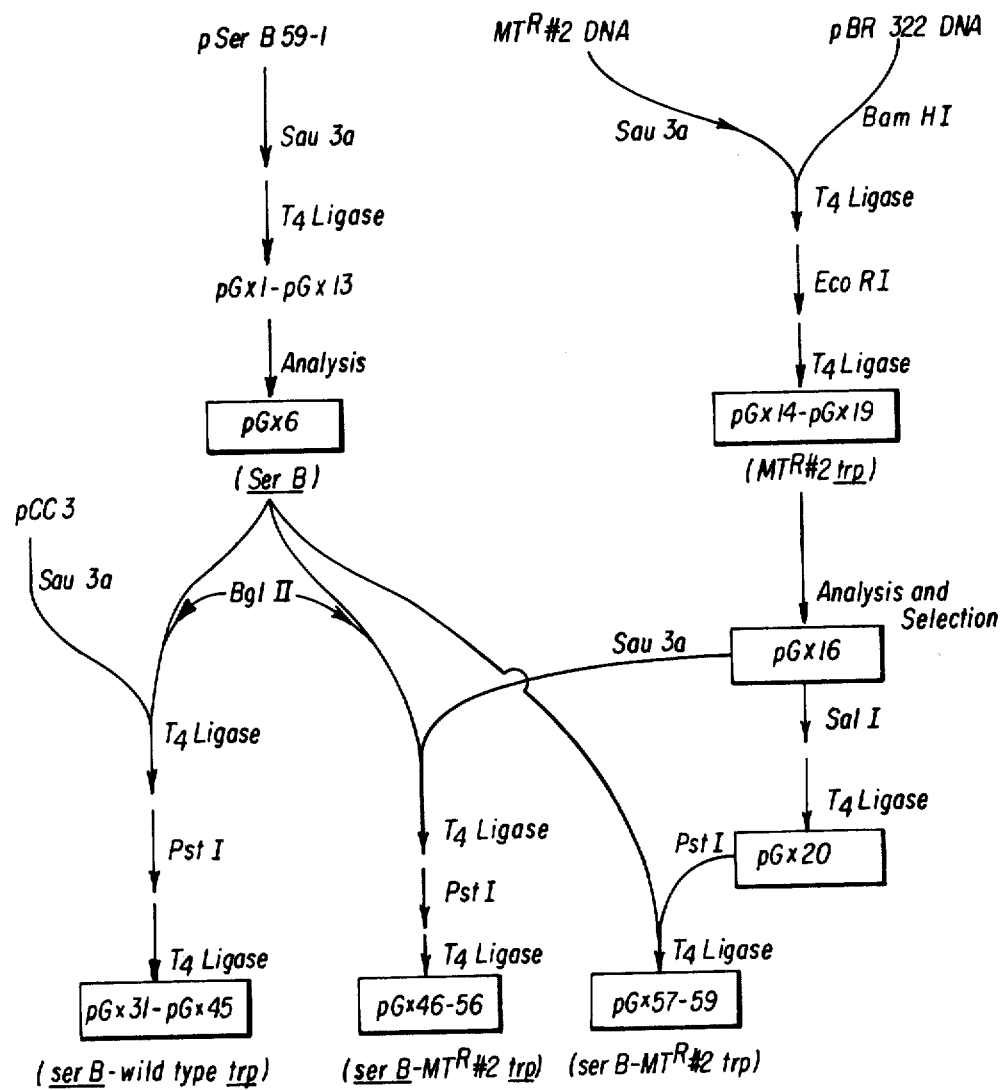

FIG. 3 is a flow chart showing the construction of composite plasmids carrying both a serB gene and a $MT^R$ #2 trpE gene. Abbreviations used:

$MT^R$ #2 trp: Methyl tryptophan resistance *E. coli* feedback resistant anthranilate synthetase.

pGx: plasmid numbering system

Figure 4:
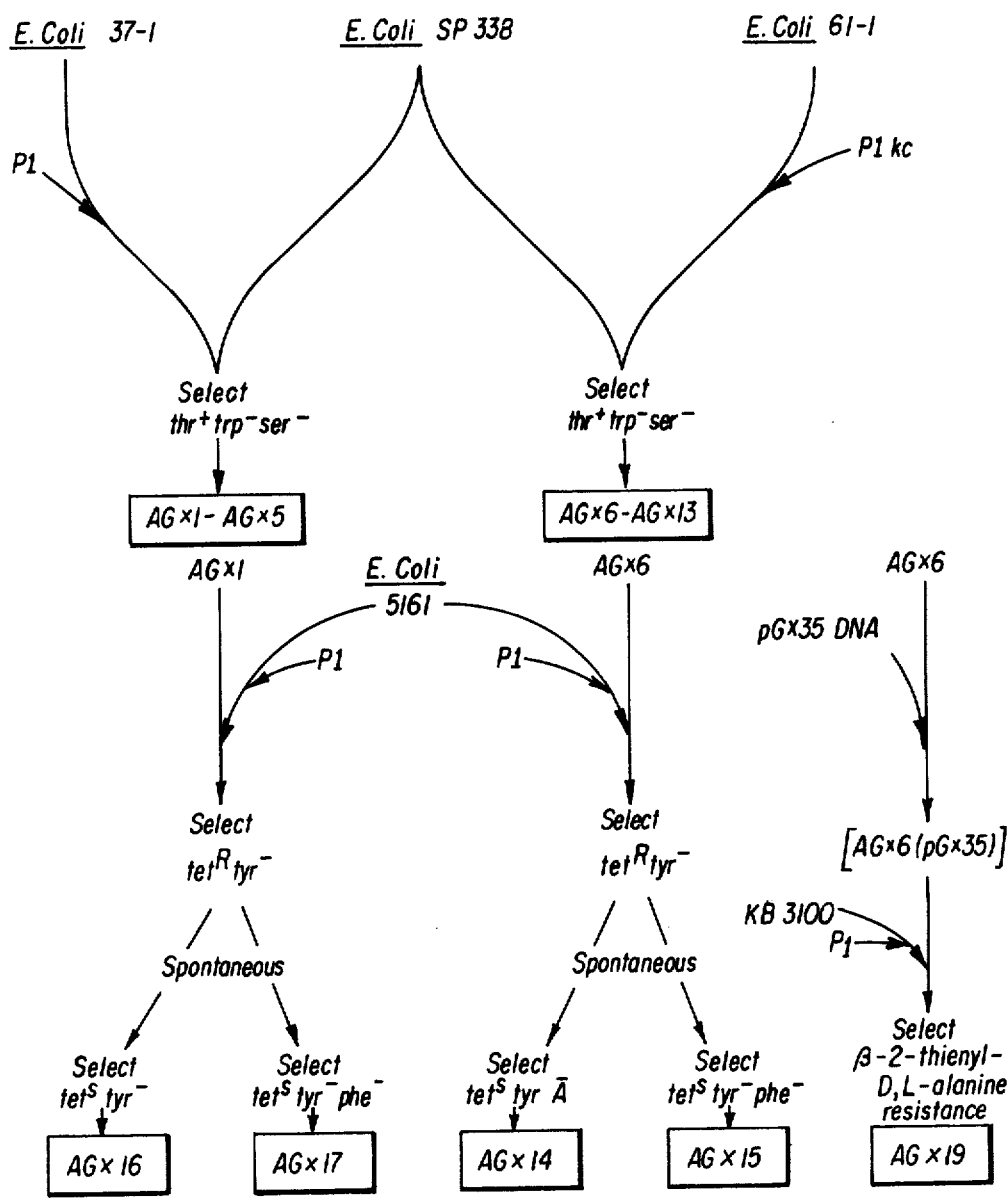

FIG. 4 is a flow chart showing the construction of host strains. Abbreviations and numbering used:

37-1: HfrH(gal-bio-attλ)$^\nabla$ deo=serB-trpR)$^\nabla$thi$^-$ strain of *E. coli*.

SP338: trpED, tna2, thr$^-$ strain of *E. coli*.

61-1: (deoB—serB)$^\nabla$thi$^-$ (gal-bio-attλ)$^\nabla$ strain of *E. coli*.

5161: tyrA: tn10 insertion strain

Pl: bacteriophage Plkc (transducing phage)

tet$^R$: tetracycline resistance

AGx: strain numbering system.

DESCRIPTION OF THE PREFERRED EMBODIMENTS

The present invention provides *E. coli* strains capable of producing high levels of L-tryptophan by fermentative procedures. The preparation of plasmids containing DNA from a donor, of the recipient strains, and of the transformants among recipients and donor DNA are as follows:

A. Plasmid Construction

The plasmids used in this invention are either stringent (single copy plasmids) or relaxed (multicopy plasmids). The multicopy plasmids are preferred since the yields of tryptophan are higher. The use of multicopy plasmids may cause instability of the resulting transformants and result in loss of the plasmids (see, e.g., Herschfield et al, supra; Hallewell, R. A., et al, Gene 9: 27–47 (1980)). However, to prevent loss, it is possible in a preferred embodiment of this invention, to add a temperature sensitive trpR gene (trpR$^{ts}$), or a trpR gene, which causes gene product synthesis to be regulated by temperature, see infra. With this gene, the stability of the multicopy plasmids carrying strains can be even further increased.

Plasmids used in this invention contain a wild type trp operon or a mutated trp operon gene which expresses feedback resistant anthranilate synthetase. In a preferred embodiment, the plasmids additionally contain a serB+ gene. Plasmids containing the trp operon or plasmids containing both a trp operon and a serB+ gene, can be constructed by using any of the well known plasmids or vectors available. These plasmids may be *E. coli* plasmids or plasmids capable of replicating in *E. coli*. Among useful plasmids, the following can be listed: ColEl, pSC101, pSF2124, pmB8, pMB9, ACYC184, pAcYC177, pCK1, R6K, pBR312, pBR313, pBR317, pBR318, pBR320, pBR321, pBR322, pBR333, pBR341, pBR345, pBR350, pBR351, pML2, pML21, ColElAp, RSF1010, pVH51, pVH151, pVH153 (Recombinant Molecules: *Impact on Science and Society:* Beers, R. F., and Bassett, E. G. eds., Raven Press, New York (1977)). Other plasmids are pBR327, pBR325 and pBR328 (Soberon, et al, Gene 9: 287–305 (1980)); still others are described in "DNA Insertion Elements, Plasmids and Episomes", Bukhari et al (eds), Cold Spring Harbor Laboratory (1977). The preferred plasmids are the multicopy plasmids of the type of pBR and its derivatives, and ColEl and its derivatives.

The presence of both serB+ and trp genes in the same plasmid assures that if, during fermentation, this plasmid is spontaneously lost, the resulting ser auxotroph bacterium will stop growing. Since some of the recipient microorganisms may be trp auxotrophs, these would naturally stop growing unless the medium contains a source of external tryptophan. However, because of the nature of the present invention, the bacteria have been producing high levels of tryptophan until the time of loss of the trp gene-containing plasmid. At the time of loss then, the medium does contain tryptophan and the plasmidless host would be able to continue growing. This would entail the undesired consumption of tryptophan from the medium and decrease overall yields of the amino acid. By constructing composite plasmids harboring both the trp+ and serB+ gene, it is assured that if a trp and ser auxotroph is used as host and if loss of the composite plasmid occurs, growth will stop and tryptophan yields will not decrease.

A plasmid containing the serB gene may be prepared, for example, from pBR322 according to Somerville (Roeder and Somerville, Molecular and General Genetics, 176: 361–368 (1979)). This plasmid called pSerB59-1 is described in FIG. 1, including the specific endonuclease sites that have been determined. The plasmid is approximately 9.4 kilo bases long and contains more genetic information than necessary. In order to decrease the size and therefore potentially increase the number of plasmid copies per cell in the final strain, it is preferred to prepare deletions of pSerB59-1. pSerB59-1 DNA can be partially digested to various extents with endonuclease Sau 3a, which cuts at the sequence

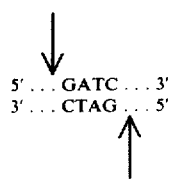

and leaves the tetranucleotide GATC single stranded on the 5' end of each fragment. Since Sau 3a has a tetrameric recognition sequence, it cuts very frequently within pSerB59-1 DNA. Partial digestion produces a somewhat random distribution of fragments representative of each segment of the plasmid. The digest can then be ligated with phage T4 ligase at low concentration to produce circles, or at higher concentrations with the endonuclease Bam HI digested pBR 322 DNA. Bam HI cuts at the hexanucleotide

Figure 1:
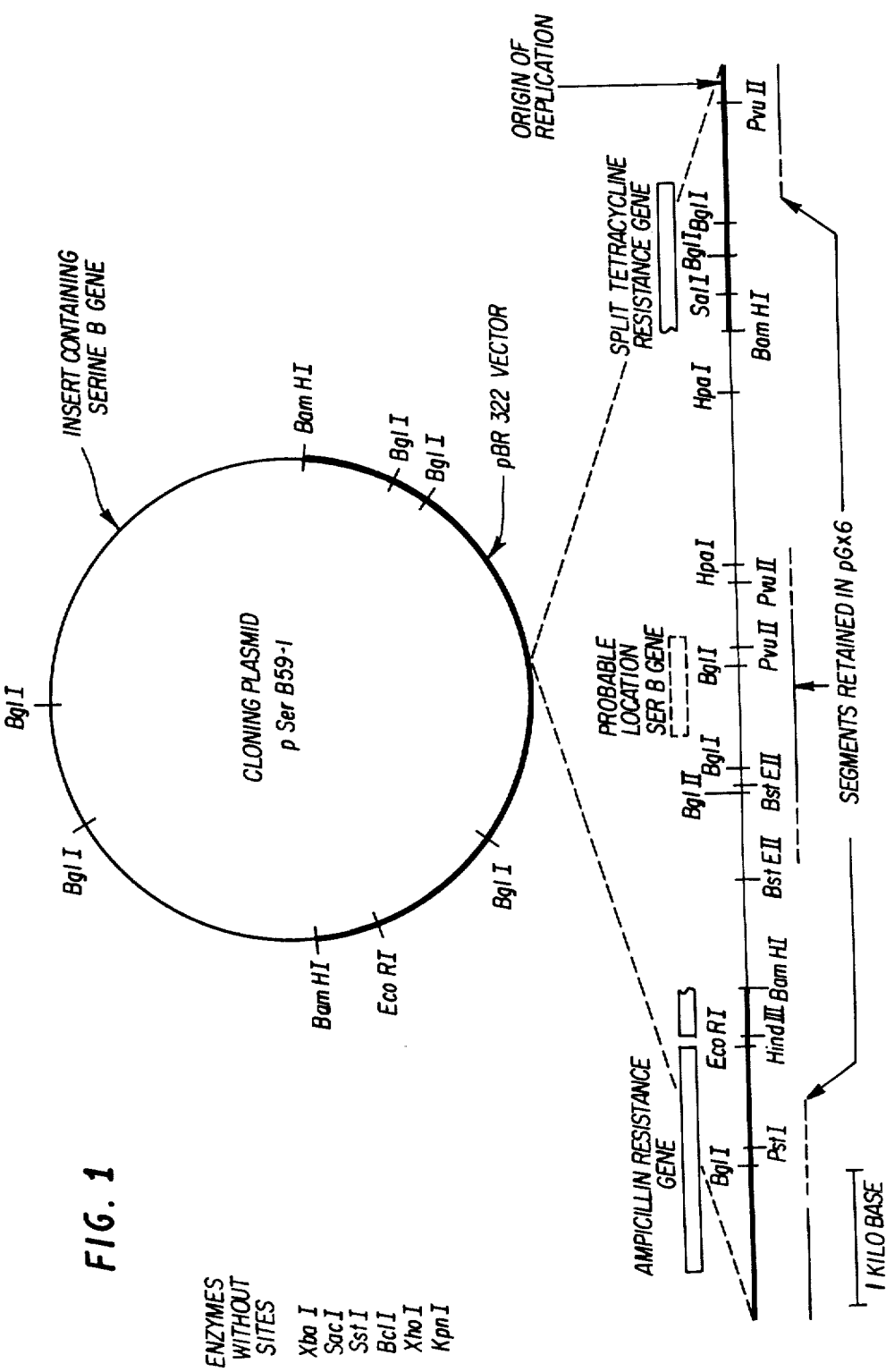
FIG. 1 shows the plasmid pSerB59-1 which is derived from the pBR322 vector and the *E. coli* serB gene. The abbreviations denote restriction endonuclease enzymes from the following sources.

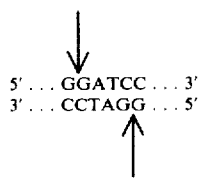

leaving the same tetranucleotide single stranded at the 5' ends of fragments as Sau 3a. Therefore, Sau 3a digested DNA can be readily ligated to Bam HI digested DNA. In order to select plasmids which carry the serB gene, the resulting mixture of deleted ligated plasmids can be introduced into a serine auxotroph and tested for colonies which grow in the absence of serine. For example, strain 37-1 E. coli W3110, HfrH, (gal-bio-attλ)$^\nabla$ (deo-serB-trpR)$^\nabla$, thi−, (Roeder and Somerville, Molecular and General Genetics 176: 361–368 (1979)) can be transformed for this purpose. Plasmids carrying the serB gene can then be isolated by screening the colonies (Eckhardt, T., Plasmid, 1: 584–588 (1978)). By such procedures, several plasmids can be isolated which are smaller than pSerB59-1 having observable deletions in the range of 85 to 51% the size of pSerB59-1. An analysis of these smaller plasmids for expression of ampicillin resistance, size and restriction sites allows the search and selection of the most efficient cloning vehicle. For example, two plasmids, having 45% the size of pSerB59-1, and a size of about 4.2 kilo bases can be isolated. Both of these have no Eco RI sites, 2 Bgl I sites, 1 Bst EII site, 1 Bgl II site, no Sal I sites and 1 Pst I site. The restriction map of a plasmid derived from pBR322 carrying a serB+ gene is also shown in FIG. 1 including the probable location of the serB+ gene in the plasmid. It can be ascertained that the enzymes Pst I and Bgl II can be used to insert genes into this plasmid. The Pst I site is located in what remains of the ampicillin resistance gene. Although the Bgl II site seems to have been preferentially retained in the deleted plasmids, it is not located within the serB gene. This can be shown by cloning Sau 3a digested cell DNA into the Bgl II site of the plasmid 6 and demonstrating that the serB+ gene function is retained. This plasmid is exemplary only. In a preferred embodiment however, this plasmid is utilized as the cloning vehicle.

Two types of trp operon genes can be used alone in plasmids, or inserted into serB gene-containing plasmids, such as those described above: (a) wild type trp operon and (b) feedback resistant anthranilate synthetase trp operon. The latter mutant trp gene is one wherein anthranilic acid synthetase is resistant to feedback inhibition by tryptophan. It can be found in high frequency in mutants resistant to tryptophan-antagonists. These antagonists inhibit the growth of Escherichia strains, but the inhibition is suppressed partially or completely when tryptophan is in the medium. Examples of tryptophan antagonists are: 4-fluoro-tryptophan, 5-fluoro-tryptophan, 6-fluoro-tryptophan, 7-fluoro-tryptophan, 4-methyl-tryptophan, 5-methyl-tryptophan, 6-methyl-tryptophan, 7-methyl-tryptophan, naphthyl-alanine, indole-acrylic acid, naphthyl-acrylic acid, β-(2-benzo-thienyl)-alanine, styryl-acetic acid, indole and tryptazan. In addition, the plasmids may be constructed so that they contain a deletion of the attenuator region of the trp operon. (Oxender et al, Proc. Nat. Acad. Sci. USA., 76: 5524 (1979)). This region is present between the operator region and the beginning of the trpE gene. With the attenuator region in place and in the presence of excess tryptophan and functional tRNA$^{trp}$, only one transcript in eight proceeds past the termination region in the tryptophan leader. Removing this control greatly increases the levels of trp operon enzymes. The absence of prematurely terminated transcripts saves metabolic energy which can be used in tryptophan production.

The feedback resistant trp genes can be cloned by partially or totally digesting the E. coli mutant trp operon with any endonuclease that does not cut within the trp operon and then ligating (e.g., using T4 DNA ligase) with plasmid at a concentration so that the cell fragments and plasmid fragments are at approximately equal molar concentration. FIG. 2 exemplifies such a technique using MT$^R$#2 (Somerville, R. and Yanofsky, C., J. Mol. Biol., 11: 747 (1965)) as donor for cell DNA and pBR322 as the plasmid. A first ligation can preferably be carried out at high DNA concentration so that formation of long concatenated molecules predominates. The resulting DNA is digested with an enzyme that cuts in the vector but not in the trp operon DNA, diluted to low concentration and religated; the low concentration favors circle formation. Detection and selection of mutant trp operon-containing plasmids can be done by transforming a (trpA-E)$^\nabla$ strain (Zalkin, H., et al, J. Biol. Chem., 249: 465–475 (1974)) therewith and allowing the cells to grow on minimal media. Resistance to 5-methyltryptophan is a property of the trp operon of the MT$^R$#2 strain. The resulting plasmids can then be used for recombining the feedback resistant trp operon into the serB+ containing plasmids, described previously. The MT$^R$#2 trp+ operon is only exemplary and any feedback resistant anthranilate synthetase expressing gene can be used.

Recombination of mutant trp operon (e.g., MT$^R$#2) containing plasmids with serB-containing plasmid yields trp+-ser+ composite plasmids. For example, partial digests of MT$^R$#2 trp-containing DNA can be ligated (T4 DNA ligase) at high DNA concentrations with excess digested serB+-containing plasmid DNA. The high molecular weight ligated DNA can be digested, with a second enzyme which does not cut in the trp operon, diluted to low concentration and ligated again to form circles. The resulting plasmids are selected by transforming E. coli cells having trp and ser deletions, so serB+/mutant trp-containing plasmids will confer on these cells the ability to grow in the absence of external tryptophan and serine. Analogous plasmids prepared from serB+ gene-containing plasmids, and wild type trp operon-containing plasmids such as pCC3 (Collins, C. J., Proc. Nat. Acad. of Sci., USA 73: 3838 (1976)) can also be prepared and tested in the same manner. The wild type or trp+ operon genes can also be obtained directly from a chromosone. The composite plasmids contain both the serB+ and wild or mutant trp gene integrated therein.

B. Host Strain Constructions

As the recipient microorganism for the hybrid DNA plasmids, tryptophanase-deficient mutants of *E. coli* are used in this invention. Preferably trp operon-lacking strains (trp operon$^\nabla$) and/or nonrevertable tryptophanase-mutated (tna) strains are used. The lack of tryptophanase insures that tryptophan is not broken down and yields of excreted L-tryptophan remain high. A tryptophan auxotroph may also be used as the recipient, since a transformant which produces tryptophan can be easily selected from the recipients. The host may also be a serine auxotroph when the serB+ gene is on the plasmid. Desirably, the host also has one or more of the following genetic deficiencies: (i) aroP gene: this gene controls the permeability characteristics of the cells to aromatic amino acids. In aroP mutant strains tryptophan excretion is proportional to anthranilate synthetase activity; (ii) trpR gene (tryptophan repressor gene): this gene controls the repression of the tryptophan biosynthetic pathway; in trpR mutant strains the pathway proceeds derepressed regardless of the levels of tryptophan produced; (iii) The trpR gene can also, in a preferred embodiment, be temperature sensitive, i.e., trpR$^{ts}$. In such case, when the cells are maintained at low temperatures trp repressor will be produced to allow normal cell growth. During production, when the cell mass has proceeded to a sufficient level, the fermentation cooling is turned off, the temperature rises and inactivates the repressor, preventing further functional trpR product synthesis: (iv) tyrA: this gene controls the biosynthetic pathway for the formation of tyrosine; in tryA mutant strains the flow of aromatic precursor (chorismic acid) can be diverted into the trp and the phenylalanine paths; (v) pheA: this gene controls the biosynthetic pathway for the formation of phenylalanine; in pheA mutant strains the flow of aromatic precursor (chorismic acid) can be diverted into the trp and tyr pathways; (vi) tyrA pheA: controls both the phenylalanine and tyrosine pathways.

Preferably the host strain may contain more than one of the aforementioned mutations in order to maximize the biosynthetic flow and excretion of tryptophan.

In order to prepare trp operon$^\nabla$ strains, it is possible to use a trpED 102 deletion strain. A threonine auxotroph with the trpED deletion, *E. Coli* SP338 (trpED$^\nabla$ 102, tna2, thr−) (Roeder and Somerville, Molecular and general Genetics, 176: 361–368 (1979)), is transduced with phage Pl lysates (Rosner, J. L., Virology 49: 679–689 (1972)) prepared on either *E. Coli* 61-1 (Roeder and Somerville, Molecular and General Genetics, 176: 361–368 (1979)) [deob-serB), thi−, (gal-bio-attλ)$^\nabla$] or on *E. Coli* 37-1 (Roeder and Somerville, supra.) [HfrH, (gal-bio-attλ)$^\nabla$ (deo-serB-trpR)$^\nabla$, thi−]. Tryptophan auxotrophs are selected which no longer require threonine and have become serine auxotrophs. They can be prepared with the trpR− 37-1 cell line Pl lysates and with trpR+ 61-1 cell line lysates.

The trpR$^{ts}$ variant can be obtained from a trp-lac fusion *E. coli* strain, (Reznikoff et al J. of Bact., 109: 526–532 (1972)), by transducing a Pl lysate thereof into any of the wild *E. coli* or mutant *E. coli* strains of this invention. In trp-lac fusion strains, trpR$^{ts}$ mutations can be readily identified.

The aroP mutation (Kuhn, J. C. and Sommerville, R. L., Biochem. Biophys. Acta 332: 298–312 (1974); Brown K. D., J. Bact. 106: 70–81 (1971)) can be inserted into trpR+ 61-1 *E. coli* by Pl transduction from *E. coli* KB 3100 (Brown, K. D., J. Bacteriol. 106: 71–81 (1971)) and selection for resistance to β-2-thienyl-DL-alanine (Brown, K. D., J. Bact. 104: 177–188 (1970)).

When trp-ser deleted cells contain one of the trp-ser plasmids, and are not supplemented with tryptophan, inhibition of growth by β-2-thienyl-DL-alanine is sufficient to allow selection of an aroP mutant. A phage Pl lysate of *E. coli* KB 3100 (arop−) can be used to infect the plasmid-containing trp ser deleted strain and the resulting colonies which grow rapidly on β-2-thienyl-DL-alanine plates are selected. One of the rapidly growing strains having an enhanced ability to excrete tryptophan can be ascertained to contain the aroP mutation.

The tryA and tryA-pheA mutations can be introduced into the strains using a strain of *E. coli* (*E. coli* 5161), which has a Tn10 transposable element (Kleckner, N. et al. Proc. Nat. Acad. Sci. USA 73: 3838–3842 (1976)) inserted in the tyrA locus. Phage Pl lysates of such *E. coli* are used to transduce trpR+ and trpR− strains. Tetracycline resistant tyrosine auxotrophs (tet$^R$tyr−) are selected. Tetracycline sensitive derivatives are selected by ampicillin enrichment (Miller, J. H., Experiments in Molecular Genetics (1972), supra) or by plating under conditions that only allow tet$^s$ colonies to grow. In this way, genes with tn10 insertions are converted to non-revertable mutations. By screening the tet$^s$ colonies, cells can be found with deletions or rearrangements that affect either the tyrA locus alone, or both the tyrA and pheA loci. The double mutants occur because the pheA map location is very close to tyrA (Bachmann, B. J. and Low, K. B. Microbiological Reviews: 44: 1–56 (1980)).

C. Transformation of Host Strains

Hosts are transformed with plasmid DNA (containing wild type trp-, wild type trp-ser, mutant trp, mutant trp-serB as well as plasmids with the attenuator deletion) by calcium shock. This procedure makes the hosts competent for DNA uptake (see, e.g., Morrison, D. A., J. Bact. 132: 349–351 (1977)). Anthranilate synthetase specific activity determinations are made with cultures of plasmid-containing cells. Alternatively, tryptophan levels can be detected enzymatically or by microbioassay. The cells are grown in a medium containing casamino acids which is tryptophan-free but contains serine, or a synthetic medium which contains all amino acids except serine and tryptophan. Strains with multicopy plasmids containing only trp genes have considerable elevations in anthranilate synthetase. In trpR+ strains, feedback resistant mutant trp-containing plasmids display a considerable increase in anthranilate synthetase specific activity over the level observed in wild-type *E. coli* W3110.

Tryptophan excretion experiments show that those strains which contain either the aroP mutations or the tyrA, tyrA pheA mutations do excrete tryptophan. Without these mutations, very little tryptophan is made, less than 10 μg/ml. High yields of tryptophan may be obtained by combining the aroP mutated hosts with a mutant trp-serB plasmid or a wild type trp-serB plasmid.

The methods of culturing the L-tryptophan producing strains thus obtained are conventional, and are similar to the methods for the cultivation of known L-tryptophan producing microorganisms. Thus, the culture medium employed is one containing carbon sources, nitrogen sources, inorganic ions and, when required, minor organic nutrients such as vitamins or amino acids. Examples of suitable carbon sources include glucose, lactose, starch hydroysate and molasses. Gaseous ammonia, aqueous ammonia and ammonium salts and other nitrogen containing materials can be used as the nitrogen source.

Cultivation of the recombinant microorganisms is conducted under aerobic conditions, in which the pH and the temperature of the medium are adjusted to a suitable level, and continued until the formation of L-tryptophan ceases.

The L-tryptophan accumulated in the culture medium can be recovered by conventional procedures (Japanese Published Unexamined Patent Application No. 74293/1979).

By the method of the present invention, L-tryptophan can be produced in higher yields than has been achieved in previously known methods using mutants of Escherichia.

Having generally described this invention, a further understanding can be obtained by reference to certain specific examples which are provided herein for purposes of illustration only and are not intended to be limiting unless otherwise specified.

A. Experimental Methods

Table 1 shows strains and plasmids used for the following experiments:

TABLE I

| | Origin of Strains and Plasmids | |
|---|---|---|
| | Description | Reference |
| 122-1(pSerB59-1) | E. coli Bam HI DNA fragment cloned in Bam HI site of pBR322 | (a) |
| pCC3 | trp operon derived from φ80ptA-E cloned in Col El along with gal operon genes | (b) |
| $MT^R$ #2 | Mutant with feedback resistant anthranilate synthetase | (c) |
| 37-1 | (serB-trpR)$^\nabla$ strain | (a) |
| 61-1 | serB$^\nabla$ strain | (a) |
| 5161 | tyrA: tn10 insertion strain | (d) |
| SP338 | trpED$^\nabla$, tna2, thr$^-$ | (a) |
| KB3100 | aroP strain | (e) |

(a) Roeder, W. and Somerville, R., Molecular & General Genetics, 176: 361-368 (1979)
(b) Collins et al, Proc. Nat. Acad. Sci. 73: 3838-3842 (1976)
(c) Pabst et al, J. Biol. Chem., 248: 901-914 (1973)
(d) Kleckner, N., et al, J. Mol. Biol. 127: 89-115 (1976); also see reference (b)
(e) Brown, K.D., J. Bact. 132: 177-188 (1970)

The following strains were deposited at the NRRL, Peoria, Ill., USA on Aug. 14, 1980:

| E. coli 37-1 | NRRL B-4568 |
|---|---|
| E. coli SP 338 | NRRL B-4569 |
| E. coli 61-1 | NRRL B-4570 |
| E. 5161 | NRRL B-4571 |
| E. coli MT® #2 | NRRL B-4572 |
| E. coli AE1 | NRRL B-4573 |
| E. coli KB3100 | NRRL B-4574 |
| E. coli trp-lac fusion | NRRL B-4575 |

MEDIA FORMULAS

| FUSZIN PLATES per liter | LB per liter |
|---|---|
| agar 15g | |
| Difco® tryptone 10g | tryptone 10g |
| Difco® yeast extract 5g | yeast extract 5g |
| sodium chloride 10g | sodium chloride 10g |
| glucose 2g | |
| chlorotetracycline 50mg | LB plates = LB + 1% agar |
| $NaH_2PO_4.H_2O$ | LB Mg = LB + 0.01M $MgCl_2$ |
| | LB Ca = LB + 0.005M $CaCl_2$ |
| autoclave, cool, then add | LB Topagar = LB + 0.75% agar |
| 6ml 2mg/ml fusaric acid | Saline = 0.85% NaCl |
| 5ml Zinc chloride 20mM | |

| Minimal plates per liter | Supplements to Minimal Plates |
|---|---|
| $K_2HPO_4$ 10.5g | amino acids 20 μg/ml |
| $KH_2PO_4$ 4.5g | tetracycline 25 μg/ml |
| $(NH_4)_2SO_4$ 1.0g | β-2-thienyl-DL-alanine 22 μg/ml |
| Sodium citrate.$2H_2O$ 0.5g | Difco® casamino acids 0.4% |
| glucose 4g | |
| (autoclave separately) | |
| agar 1.5g | biotin 1 μg/ml |
| (autoclave separately) | |
| after cooling adjust to | thiamim 1 μg/ml |
| $MgCl_2$ 1mM | |
| $Fe_2SO_4$ 10 μM | |

| Solutions for Transformations | |
|---|---|
| Wash: | 100mM NaCl |
| Solution: | 5mM $MgCl_2$ |
| | 5mM Tris HCl pH 7.6 |
| Calcium Solution: | 100mM $CaCl_2$ |
| | 250mM KCl |
| | 5mM $MgCl_2$ |
| | 5mM Tris TCl pH 7.6 |

M9 casamino acids medium
per liter

| casamino acids | 4g |
|---|---|
| $Na_2HPO_4$ | 6g |
| $KH_2PO_4$ | 3g |
| NaCl | 0.5g |
| $NH_4CL$ | 1.0g |

Make 0.1mM in CaCl and 0.4% glucose after autoclaving

| Solutions for DNA Preparation | | |
|---|---|---|
| Wash: | A | 0.2M Tris/HCl pH 8.0 |
| | | 0.8% NaCl |
| | | 0.01M EDTA |
| Buffer: | B | 50mM Tris pH 8.0, 20% sucrose |
| Buffer: | C | 0.25M EDTA pH 8.0 |
| Lysozyme A | | 5 μg/ml lysozyme in 0.25M Tris/HCl pH 8.0 |
| Lysozyme B | | 10 μg/ml lysozyme in 0.25M Tris/HCl pH 8.0 |
| Lysis Buffer: | | 60mM EDTA |
| | | 5mM Tris |
| | | 0.1% Triton X-100 |
| Buffer: | D | 20% sucrose |
| | | 0.1M NaCl |
| | | 0.01M Tris pH 8.0 |
| SDS Buffer E: | | 50mM Tris pH 8.0 |
| | | 20mM EDTA |
| | | 10% SDS |
| Buffer F: | | 10mM Tris |
| | | 1mM EDTA pH |

Construction of Specific Plasmids

FIG. 3, shows a flow chart for the construction of serB-trp+ containing plasmids pGx 31–59. Cells containing plasmids (such as e.g., pGx6, pCC, pGx16 or pGx20) were grown at 37° C. in M9 casamino acid medium (sometimes with the addition of ampicillin to 100 μg/ml) to an O.D.550 of 1.0 then made 100 μg/ml in chloramphenicol. The cultures were further incubated at 37° C. for approximately 10 to 15 hours, cells harvested by centrifugation at 8,000 RPM for 5 minutes, resuspended in wash A and recentrifuged. The cell pellet was sometimes frozen at this point. The cells from one liter of culture were suspended in 15 ml of buffer B, 3 ml of lysozyme A solution and 6 ml buffer C was added and incubated on ice until spheroplast cells formed. Lysis buffer was added (12 ml) and the mixture incubated at 37° C. for 10', then cooled on ice and centrifuged 20,000 RPM for 40 minutes. The plasmid containing supernatant was made 0.02 mg/ml ethidium bromide, mixed with an equal weight of CsCl and centrifuged 40,000 RPM to equilibrium in a vertical or angle ultracentrifuge rotor. The supercoiled plasmid DNA band was collected, ethidium bromide was extracted with isopropanol saturated with 4 M NaCl, the DNA precipitated with ethanol and redissolved in buffer E. The yield is generally 500-800 μg DNA per liter of cultured cells.

Isolation of chromosomal DNA from E. coli $MT^R\#2$. A single colony growing on a minimal agar plate supplemented with 5 methyl tryptophan was picked and grown in 5 ml of LB overnight. This was incubated into 1 liter of LB medium and grown to an O.D.550 of 1.0. The cells were centrifuged, washed with saline and frozen at $-20°$ C. The cells from 1.5 liters were thawed in buffer D, (20 ml) and 4 ml of lysozyme B solution (4 ml) was added and incubated at 37° C. When greater than 90% of the cells had formed spheroplasts, SDS buffer (20 ml) was added and the cells were mixed until completely lysed. Proteinase K (2 mg) was added and the solution was incubated at 50° C. for 30 minutes. The DNA was extracted by mixing with phenol-chloroform (1:1) and centrifuged at 8000 RPM for 10 minutes.

Extractions were repeated until no interface remained between the aqueous and phenolic layers after centrifugation. The DNA solution was extracted with ether 3X then dialyzed vx. buffer F overnight. The DNA was precipitated by making the solution 0.2 M sodium acetate (pH 5.0), adding 2.5 volumes of ethanol cooling at $-20°$ C. and centrifugation at 8000 RPM for 10 minutes. The DNA was dissolved in buffer F.

Restriction endonuclease digestions were performed with enzymes purchased commercially. The digestion conditions used were those recommended by the manufacturers. Generally 2-10 μg of DNA were digested in 20 to 100 μl of buffer with 2 to 10 units of enzyme at 37° C. for 1 hour. The partial digestions with Sau 3a were performed with approximately 0.05 units of enzyme per μg of DNA for generally 10 to 20 minutes. The molecular weight size range of the partially digested DNA was assessed by agarose gel electrophoresis.

Ligations were performed with T4 ligase purchased commercially. The buffer conditions were those recommended by the manufacturer. High DNA concentration ligations were performed by precipitating together in one tube approximately 5–10 μg of vector DNA with 12–15 μg of partially digested DNA and dissolving and ligating in 20 μl of ligation buffer. The second ligation (low DNA concentration) of these samples after endonuclease digestion was performed at a 25 fold dilution in DNA concentration. Other ligations were performed with 1.6 μg DNA per 50 μl ligation mixture and 0.5 μg DNA per 100 μl ligation mixture respectively.

Table II shows $MI^R \#2$ trp containing plasmids and Table III shows composite plasmids containing wild or $MT^R \#2$ trp+ operon and serB+ genes. Table III also shows transformations effected with the composite plasmids.

TABLE 1

Analysis of $MT^R \#2$ trp Recombinants[1]

| Plasmid | Number of Restriction Sites | | Estimated Size (Kb) |
|---|---|---|---|
| | BamHI | SALI | |
| pG × 14 | 3 | 4 | 33 |
| pG × 15 | 3 | 4 | 33 |
| pG × 16 | 1 | 2 | 19 |
| pG × 18 | 3 | 4 | 33 |
| pG × 19 | 2 | 3 | 20 |

[1]Constructions shown in FIG. 3.

TABLE II

Characteristics of trp-ser Plasmids Derived with Sau3a Digests

| Plasmid | Derivation pCC3 | Derivation pG × 16 | Ampicillin Resistance | Approx. Size Kb | (trp A-E)[V] Strain[2] | Transformations[1] CSH 27[3] | 37-1 | AGx-6 | AGx-1 | SP338 |
|---|---|---|---|---|---|---|---|---|---|---|
| pG × 31 | X | | Sensitive | 11.4 | Yes | | | | | |
| 32 | X | | Sensitive | 11.0 | Yes | | | | | |
| 35 | X | | Sensitive | 10.0 | No | No | Yes | Yes | Yes | Yes |
| 37 | X | | Sensitive | 9.7 | No | | | | | |
| 40 | X | | Sensitive | 12.5 | Yes | | | | | |
| 43 | X | | Sensitive | 9.7 | No | | | Yes | | Yes |
| 44 | X | | Sensitive | 11.0 | Yes | Yes | | Yes | | |
| 47 | | X | —* | 6.5,10,12.2 | Yes | Yes | Yes | Yes | Yes | Yes |
| 48 | | X | Resistant | 8.4 | No | No | Yes | Yes | Yes | Yes |
| 49 | | X | Resistant | 9.3 | No | | Yes | Yes | Yes | |
| 50 | | X | Resistant | 12.2 | Yes | Yes | | Yes | Yes | Yes |
| 51 | | X | Resistant | 9.7 | No | | Yes | Yes | Yes | |
| 52 | | X | — | 9.3 | Yes | | Yes | | Yes | |
| 53 | | X | — | 10.5 | No | Yes | Yes | Yes | Yes | Yes |
| 55 | | X | — | 9.3 | No | | | | Yes | |

*—means not tested
[1]For host strain construction and nomenclature see, supra.
[2](trp A-E)[V] strains are described in e.g., Zalkin, H. et al, J. Biol. Chem., 249:465-475 (1974).
[3]Experiments in Molecular Genetics, Cold Spring Harbor Laboratory, 1972, Cold Spring Harbor, NY 11714, (p.17), available in a kit.

The preparation of calcium shocked cells and transformation are described in the section infra on strain construction.

Construction of Specific Strains

FIG. 4, shows a flow chart for strain construction. All strain constructions were performed using transduction with phage Plkc and in some cases the transposon Tn10 was also used. All Plkc lysates were prepared according to the procedure of Rosner (J. L. Virology 49: 679-689 (1972). Basically, 3 ml of an overnight culture grown in LB Mg medium from a single colony of the bacteria of interest was made 5 mM CaCl$_2$ and incubated with 0.1 ml of a previous Plkc lysate (~titer=3×10$^8$ pfu/ml prepared with W3110) at 37° C. for 30 minutes. Ten ml of LB Mg broth and 10 ml of LB top agar (molten at 45° C.) were added and approximately 7.5 ml of the mixture was poured onto LB Ca plates. The plates were incubated at 37° C. for approximately 8 hours. The top agar was removed, sterilized with chloroform and centrifuged to remove agar and cell debris. The lysates were titered using SH16 Shigella strain as indicator.

Transduction experiments were also performed according to Rosner, supra. An exponentially growing culture of the recipient bacteria in LB medium was made 10 mM CaCl$_2$. The culture was mixed with an equal volume of Plkc plate lysate and incubated for 30 minutes at 37° C. This culture was washed and resuspended in saline and spread on selective plates. For infection of E. coli SP338, minimal agar plates with glucose, serine and tryptophan were used to select against non-transduced SP388 which requires threonine. These strains were then screened by replica plating to be sure they were serine and tryptophan auxotrophs.

In infection of strains like [AG×6(pG×35)] with KB3100 Pl lysates, transductants were selected by spreading on plates containing β-2-thienyl-DL-alanine. In infections of AG×6 and similar strains with 5161 Pl lysates, cultures were plated on minimal agar plates containing glucose, tetracycline, tryptophan, serine and tyrosine. The resulting colonies were replica plated onto plates without tyrosine to be sure they were tyrosine auxotrophs.

Non-revertable mutations were obtained in the tyrA and pheA genes by screening for auxotrophs after spontaneous loss of the Tn10 transposon. The procedures used for the manipulation of these cultures were primarily those of Kleckner et al, J. Mol. Biol. 127: 89–115 (1979). In the spontaneous selection of tet$^s$ and tyrA or tet$^s$, tyrA pheA, a single colony of tet$^R$ tyr cells was grown to approximately 2×10$^8$ cells/ml in LB medium broth. An ampicillin selection was then used to kill cells remaining tetracycline resistant. The cultures were made 10 μg/ml tetracycline grown for 60 minutes then made 200 μg/ml ampicillin and incubated for another 60 minutes. The culture was washed and resuspended in L- broth and grown overnight. The ampicillin selection was repeated and cells were plated on minimal plates containing glucose, tryptophan, serine, tyrosine and phenylalanine. These cells were replica plated to test for tyrosine or tyrosine-phenylalanine auxotrophs.

In the preparation of AG×16 and AG×17 a slightly different protocol was used to isolate tet$^s$, tyrA or tyrA-pheA mutants. Single tetracycline resistant tyrosine auxotrophic colonies were grown overnight in 5 ml LB media. An aliquot (0.1 ml) was placed on Fuszin plates (these plates only allow growth of tetracycline sensitive colonies). These colonies were replica plated onto the appropriate plates to test for ser trp tyr (AG×16), or ser trp tyr phe (AG×17) colonies.

Cells were calcium shocked to make them competent for DNA uptake by the procedure of Morrison (J. Bact. 132: 349–351 (1977). The desired cells were grown in 500 ml of LB medium to an optical density of 0.32 at 550 nm, then chilled on ice. All the following procedures were carried out at 0°–4° C. Cells were washed (centrifuged at 8000 RPM for 10 minutes and resuspended in 200 ml wash solution then centrifuged again) two times and resuspended in 200 ml of calcium solution. This was held on ice for 25 minutes, centrifuged and resuspended in 4 ml calcium solution. The cell suspension was held at 0° C. overnight, then made 20% in glycerol and frozen at −70° C. in 0.2–0.3 ml aliquots.

Transformations were performed by thawing an aliquot of the frozen calcium treated cells and adding 0.1 to 1.0 μg of purified DNA or DNA ligation mixture. The cells were held on ice for 10 minutes, heated at 37° C. for five minutes then allowed to sit at room temperature for 10 minutes. At this point the cells are either plated directly on selective plates or incubated with 3 ml of LB medium at 37° C. for 90 minutes to allow plasmid expression, washed with saline and plated on selective plates. In the case of formation of [AG×6(pG×35)] and similar transformants, the transformation mixture was plated on glucose minimal plates supplemented with casamino acids (Difco) which only allows AG×6 cells that have obtained the pG×35 plasmid to grow.

Transformations of Host Strain and Cultivation of Transformants

Transformants were prepared as described previously, and grown as follows:

Main cultures:

A loopful of grown cells on above media was inoculated into the following L-tryptophan production media (3 ml per test tubes each) and cultured at 30° C. for 3 days (70 hr) with shaking.

The composition of L-tryptophan production medium is as follows: glucose 3%, (NH$_4$)$_2$SO$_4$ 1%, KH$_2$PO$_4$ 0.1%, MgSO$_4$, 7 aq 0.1%, FeSO$_4$, 7aq 0.001%, MnCl$_2$.4aq 0.001% "Casamino acid" (Difco$^R$, vitamin free) 0.4%, CaCO$_3$ 4.0% pH 7.0 with KOH.

Detection and determination of L-tryptophan:

L-tryptophan in culture broth was detected qualitatively by Ehrlich reagent spray onto spots put on filter paper. Samples which gave tryptophan spots, were tested for quantitative determination of L-tryptophan by microbioassay with *Leuconostoc mesenteroides*.

Determination of growth:

Growth was determined by optical density at 562 nm (10 mm glass cell) after dilution of culture broth 26 fold with 0.1 N HCl. Relative values are indicates as −, ±, +, ++.

Table IV indicates some of the successful transformants and the growth results:

TABLE IV

| Ex. | Transformant | Host | Plasmid | Growth | L-trp(μg/ml)[a] |
|---|---|---|---|---|---|
| (1) | [AG × 6(pG × 35)aroP] | tna, trpR+, aroP | wild type trp-serB | ± | 230, 302[b], 186[b](*) |
| (2) | AG × 16(pG × 35) | tna, trpR−, tyrA | " | − | 270[b] |
| (3) | AG × 6(pG × 35) | tna, trpR+ | " | ++ | 280[b] |
| (4) | AG × 1(pG × 35) | tna, trpR− | " | ++ | 104 |
| (5) | AG × 14(pG × 35) | tna, trpR+, tyrA− | " | ± | 211 |
| (6) | AG × 14(pG × 44) | tna, trpR+, tyrA− | " | ± | 102 |

TABLE IV-continued

| Ex. | Transformant | Host | Plasmid | Growth | L-trp(μg/ml)[a] |
|---|---|---|---|---|---|
| (7) | AG × 15(pG × 35) | tna, trpR+, tyrA−, pheA | " | ± | 155 |
| (8) | AG × 15(pG × 44) | tna, trpR+, tyrA−, pheA | " | + | 241 |
| (9) | AG × 17(pG × 44) | tna, trpR−, tyrA, pheA | " | − | 48 |

[a]cultured for 3 days and determined at end of period of cultivation, unless otherwise stated.
[b]cultured for 3 days, stored at 25–30° C. for 5 days and at 4° C. for 3 days, then determined.
(*) A yield as high as 760 μg/ml was obtained in one determination.

The following strains were deposited at the Northern Regional Research Laboratory (NRRL), Peoria, Ill., USA, on Aug. 14, 1980

| | |
|---|---|
| AG × 6(pG × 35) aroP | NRRL B-12257 |
| AG × 16(pG × 35) | NRRL B-12258 |
| AG × 6(pG × 35) | NRRL B-12259 |
| AG × 1(pG × 35) | NRRL B-12260 |
| AG × 14(pG × 44) | NRRL B-12261 |
| AG × 15((pG × 44) | NRRL B-12262 |
| AG × 17(pG × 44) | NRRL B-12263 |
| AG × 6(pG × 50) (aroP) | NRRL B-12264 |

AG×6 (pG×50) aroP is an example of a strain of the following genotype: tna, trpR−, tyrA−, aroP (MT$^R$#2 trp-Serb)

What is claimed as new and intended to be covered by Letters Patent of the United States is:

1. A bacterium which comprises a host of the genus Escherichia deficient in the enzyme tryptophanase carrying a plasmid with genetic information to control tryptophan production, wherein said host is resistant to a tryptophan analog.

2. A bacterium which comprises a host of the genus Escherichia deficient in the enzyme tryptophanase carrying a plasmid with genetic information to control tryptophan production, which host additionally carries a gene deficiency selected from the group consisting of trpR, aroP, pheA and combinations thereof.

3. The bacterium of claim 1 wherein said analog is selected from the group consisting of 5-methyltryptophan, 5-fluoro-tryptophan, 4-methyl-tryptophan, 4-fluoro-tryptophan, 6-methyl-tryptophan, and 6-fluoro-tryptophan.

4. The bacterium of any of claims 1 or 2, wherein said host is a tryptophan auxotroph.

5. The bacterium of any of claims 1 or 2 wherein said host is a serine auxotroph.

6. The bacterium of claim 4 wherein said host is also a serine auxotroph.

7. The bacterium of claim 1 which additionally carries a trpR$^{fs}$ gene alone or in combination with a gene deficiency selected from the group consisting of aroP, tyrA, pheA, and combinations thereof.

8. The bacterium of claim 2 wherein said gene deficiency is aroP.

9. The bacterium of claim 2 wherein said gene deficiency is tyrA.

10. The bacterium of claim 2 wherein said gene deficiency is pheA.

11. The bacterium of claim 2 wherein said gene deficiency is tyrA, pheA.

12. The bacterium of claim 2 wherein said gene deficiency is trpR.

13. The bacterium of claim 2 wherein said gene deficiency is a combination of trpR, tyrA, pheA and aroP.

14. The bacterium of any of claims 1 or 2 wherein said plasmid is a single copy plasmid or a multi copy plasmid.

15. The bacterium of any of claims 1 or 2 wherein said plasmid carries a gene selected from the group consisting of serB gene, wild type trp operon and combinations thereof.

16. The bacterium of any of claims 1 or 2 wherein said plasmid carries a gene selected from the group consisting of a feedback resistant anthranilate synthetase trpE operon gene and combinations thereof with a serB gene.

17. The bacterium of any of claims 1 or 2 wherein said plasmids also carry a deletion of the attenuator region of the trp operon.

18. A method of producing L-tryptophan by fermentation which comprises:
growing a bacterium which comprises a host of the genus Escherichia deficient in the enzyme tryptophanase, carrying a plasmid with genetic information to control tryptophan production in an appropriate growth medium, and collecting tryptophan from said medium;
wherein said host is resistant to a tryptophan analog.

19. A method of producing L-tryptophan by fermentation which comprises:
growing a bacterium which comprises a host of the genus Escherichia deficient in the enzyme tryptophanase carrying a plasmid with genetic information to control tryptophan production in an appropriate growth medium, and collecting tryptophan from said medium;
wherein said host additionally carries a gene deficiency selected from the group consisting of trpR, aroP, tyrA, pheA, and combinations thereof.

20. The method of claim 18 wherein said analog is selected from the group consisting of 5-methyl-tryptophan, 5-fluoro-tryptophan, 4-methyl-tryptophan, 4-fluoro-tryptophan, 6-methyl-tryptophan, and 6-fluoro-tryptophan.

21. The method of any of claims 18 or 19 wherein said host is a tryptophan auxotroph.

22. The method of any of claims 18 or 19 wherein said host is a serine auxotroph.

23. The method of claim 21 wherein said host is a serine auxotroph.

24. The method of claim 18 wherein said host additionally carries gene deficiencies selected from the group consisting of trpR, aroP, tyrA, pheA, and combinations thereof.

25. The method of claim 19 wherein said gene deficiency is aroP.

26. The method of claim 19 wherein said gene deficiency is tyrA.

27. The method of claim 19 wherein said gene deficiency is pheA.

28. The method of claim 19 wherein said gene deficiency is tyrA, pheA.

29. The method of claim 19 wherein said gene deficiency is trpR.

30. The method of claim 19 wherein said gene deficiency is a combination of trpR, tyrA, pheA and aroP.

31. The method of any of claims 18 or 19 wherein said plasmid is a single copy plasmid or a multi copy plasmid.

32. The method of any of claims 18 or 19 wherein said plasmid carries a gene selected from the group consisting of serB gene, wild type trp operon and combinations thereof.

33. The method of any of claims 18 or 19 wherein said plasmid carries a gene selected from the group consisting of a feedback resistant anthranilate synthetase trpE operon gene and combinations thereof with a serB gene.

34. The method of any of claims 18 or 19 wherein said plasmids also carry a deletion of the attenuator region of the trp operon.

* * * * *